United States Patent [19]
Becking

[11] 3,985,809
[45] Oct. 12, 1976

[54] PRODUCTION OF ANISALDEHYDE
[75] Inventor: Donald Harvey Becking, Birmingham, Mich.
[73] Assignee: Oxy Metal Industries Corporation, Warren, Mich.
[22] Filed: Jan. 15, 1975
[21] Appl. No.: 541,295

Related U.S. Application Data
[63] Continuation of Ser. No. 384,778, Aug. 1, 1973, abandoned.

[52] U.S. Cl. .............................. 260/600 R; 204/92; 260/599; 260/507 R; 260/524 S; 260/521 B
[51] Int. Cl.² ....................................... C07C 45/00
[58] Field of Search ............... 260/600, 599, 524 S

[56] References Cited
UNITED STATES PATENTS
2,450,877   10/1948   Carpenter et al. .................. 260/600
3,665,030   5/1972   d'Ostrowick et al. ........... 260/600 X FOREIGN PATENTS OR APPLICATIONS
62,426   11/1957   India ................................... 260/599

OTHER PUBLICATIONS
Ramaswamy et al., J. Electrochemical Soc., vol. 110 (1963) 202–204.
Kagami, Chem. Abstract, 68 (1968) 63033a.
Rocek, Chem. Abstract, 70 (1969) 28088d.

Primary Examiner—Bernard Helfin
Attorney, Agent, or Firm—B. F. Claeboe

[57] ABSTRACT
The present invention is directed broadly to the manufacture of aromatic aldehydes and acids, and is more specifically concerned with the preparation of anisaldehyde utilizing a manganic salt to oxidize either methoxytoluene or the benzyl or toluol sulfonic ester of p-cresol whereby under carefully controlled conditions there is obtained a minimum of tars, a minimum of aromatic acids and a minimum utilization of the methoxytoluene for conversion to anisaldehyde.

2 Claims, No Drawings

PRODUCTION OF ANISALDEHYDE

This is a continuation of application Ser. No. 384,778, Filed Aug. 1, 1973, now abandoned.

BACKGROUND OF THE INVENTION

It is known in the art that anisaldehyde can be prepared by a number of methods, one process being the oxidation of p-methoxytoluene with manganese dioxide and sulfuric acid. The literature also contains reference to a method in which there is oxidized benzyl or toluol ester of p-cresol using manganese dioxide as the oxidizing agent and to then methylate the p-hydroxy benzaldehyde which is formed. Anisaldehyde can also be prepared through the oxidation of p-hydroxy benzyl alcohol, followed by methylation. Another known process is to go through the oxidation of p-nitrotoluene to the aldehyde then the reduction to the amino group and next conversion to the hydroxy group, followed by methylation of that group to anisaldehyde. Of course, many other ways to prepare anisaldehyde are known; however, those mentioned are exemplary of the prior art.

In all the processes for preparing anisaldehyde known to applicant, at least one disadvantage exists. Typical disadvantages are their relatively high costs and/or the presence in the final product of an excessive amount of impurities.

SUMMARY OF THE INVENTION

The instant invention is based upon the discovery that when a compound such as potassium manganate alum or manganic alum in which the manganate ion has a plus 3 valence is introduced into an approximately 8 percent by weight sulfuric acid solution and p-methoxytoluene added, this particular benzene derivative undergoes a smooth and efficient oxidation reaction with the production of a high yield of anisaldehyde, or as it is also referred to in the literature p-methoxybenzaldehyde. It is important to the preparation of anisaldehyde in this fashion that the acidity be kept between 2½ and 8½ percent by weight at all times and also that the temperature of the oxidation reaction not be permitted to advance substantially beyond 30° C. It is also important that there be kept in the system a large excess of p-methoxytoluene, and when these conditions are followed, a high yield of anisaldehyde is obtained with only a minimum of tars and aromatic acids present.

As will be pointed out in greater detail hereinafter, it is also possible and practical by minor variations in this process to produce a wide range of benzaldehydes and benzoic acids. Illustratively, such compounds are parachlorobenzoic acid, parachlorobenzaldehyde, dichlorobenzoic acid, and parasulfobenzoic acid.

DESCRIPTION OF PREFERRED EMBODIMENTS

Anisaldehyde finds numerous commercial applications in perfuming, soap additives, food additives, chemical intermediates and electroplating. In the latter application, anisaldehyde is used as an additive to zinc plating solutions, thereby brightening the deposits. In this application the anisaldehyde can conveniently be used as a bisulfite complex, since it is not necessary to use this compound in the high degree of purity required in the perfumery art.

The instant invention will now be more fully understood by the following detailed description of the process. In this illustrative experiment, there was employed one four hundred and fifty gallon electrolytic cell which was operated with a five thousand ampere rectifier at 15 amperes per gallon and a voltage of about 2.8 to 4.5. Lead sheets were used as the cathode and anode at a ratio of about 1 to 3. To these cells were added requisite volumes of a solution having a concentration of approximately 160 grams per liter of manganese sulfate, 180 grams per liter of potassium sulfate and 400 grams per liter of sulfuric acid. When the manganese ion decreased to about 10 grams per liter, the dark almost black sludge from the cell was transferred to a four-thousand gallon reactor which was approximately half full of 8 percent by weight of sulfuric acid. The reactor jacket had cooling water running through it, and the next step in the process was to add seven-thousand pounds of paramethoxytoluene to the reactor. The temperature was maintained between 25° and 30° C until the ratio of the methoxytoluene to anisaldehyde lies between about 3:1 and not less than 2:1 as determined on a gas choromatograph. The solution was allowed to settle, and the clear liquid was removed from the bottom of the reactor and then transferred to a tank where it was brought up to a concentration of 160 grams per liter of manganese sulfate, 125 to 150 grams per liter of potassium sulfate and 40 percent by weight sulfuric acid. This solution was now ready to be transferred back to the electrolytic cell for reoxidation.

The solution of anisaldehyde and methoxytoluene which remained in the reaction vessel was washed with 500 gallons of 10 percent by weight sodium bicarbonate solution and allowed to settle. The bicarbonate solution was then decanted from the methoxytoluene and anisaldehyde. A saturated solution of five-hundred gallons of sodium bisulfite was added to the kettle and heated to about 120° F until all of the anisaldehyde had formed a soluble bisulfite. The carbonate solution can be acidified for separation and recovery of the anisic acid.

The anisaldehyde bisulfite was separated from the methoxytoluene by the following procedure. Three-thousand gallons of water were added to the mixture, the combined mixture heated to about 120° F with stirring for approximately 2 hours, and then allowed to settle. The methoxytoluene in the upper layer can then be recycled back to the reaction vessel. The lower layer containing the anisaldehyde bisulfite after carbon treatment may be converted to anisaldehyde by adjusting the pH to about 9 with sodium carbonate. The anisaldehyde no longer complexed with the bisulfite is immiscible with water and separated out. It is found that the product obtained averaged about 97 to 98 percent anisaldehyde and about 1 to 3 percent methoxytoluene.

If desired, during the oxidation reaction copper sulfate ($CuSO_4.5H_2O$) in the amount of approximately two pounds per 100 gallons of methoxytoluene can be added, and this salt functions as a catalyst to make the rate of oxidation uniform over the entire reaction period. The sulfate allows the reaction to proceed at an even rate with less anisic acid and tars being formed. Cobalt sulfate or cobalt acetate can also be used; however, it has been found that relatively more acid is produced with these materials. Other metal salts may of course be found effective for this purpose.

To further illustrate the invention a relatively small laboratory procedure will now be described. The black precipitate from the electrolysis, which is potassium manganic alum with a possible formula of ½(K₂SO₄).Mn₂(SO₃)₃ in the amount of one liter was placed in a twelve liter flask. The twelve liter flask contained from 6 to 6½ liter of 6 to 8½ percent by weight sulfuric acid, and to this flask was then added 2000 grams of 100 percent of p-methoxytoluene. The temperature was maintained between about 15° and 20° C for the first 4 hours, then allowed to rise to 28° to 34° C. At the end of a second four-hour period the acidity of the solution was approximately 2 to 3 percent. At this point 250 cc. of 45 percent by weight of sulfuric acid from the clear liquor in the electrolytic cell was added every 3 hours. When the sludge had disappeared, a gas choromatograph was run and the ratio of p-methoxytoluene to anisaldehyde was determined. One liter more of sludge was added and the procedure just described was repeated until the ratio of the methoxytoluene to anisaldehyde lies between about 3:1 and not less than about 2:1. If the black sludge had not disappeared and the ratio of methoxytoluene to anisaldehyde was lower than 2 to 1, more paramethoxytoluene is added. This reaction yielded between 700 and 750 grams of anisaldehyde from 2 liters of settled sludge.

The separation of the methoxytoluene-anisaldehyde mixture may be done in either one of two ways. First, the methoxytoluene-anisaldehyde layer may be separated from the manganous sulfate-sulfuric acid solution and added to three liters of saturated bisulfite solution. The methoxytoluene and anisaldehyde mixture may then be stirred at between 120° and 130° F for 3 hours, with the bisulfite. Six liters of water may then be added and again heated to 120° F, and allowed to cool. With the exception of 1 percent by weight, the anisaldehyde passes into the water layer as the bisulfite complex. The methoxytoluene now contains about 1 percent or less anisaldehyde, and may be returned for further oxidation. The bisulfite complex which is in the water layer may then be precipitated by adding an excess of sodium bisulfite to the solution and by filtering there is produced an anisaldehyde bisulfite complex which is useful in zinc plating solutions as a deposit brightener.

A second method of effecting separation of the methoxytoluene-anisaldehyde mixture is to wash it with sodium bicarbonate solution and to then distill off the excess methoxytoluene and anisaldehyde under vacuum. This produces anisaldehyde of a relatively high degree of purity which may be utilized in perfuming, soap additives, and chemical intermediates.

While applicant does not wish to be bound by a particular theory, it would appear that in the oxidation procedure, hydrogen abstraction to form an ion is the principal reaction taking place. It would seem that there is an oxidation of the methyl group and then there is an oxidation of the aldehyde group to the acid group. There occurs a slight oxidation of the methoxy group to revert to p-cresol, which then forms the tars through further oxidation products. The relative speed of these reactions is dependent upon the hydrogen ion concentration of the solutions and also the temperature under which the reaction is run. Generally speaking, the aldehydes always appear first, and depending upon the temperature and the acidity, the aldehydes may remain as aldehydes or they may be oxidized further to the benzoic acid. In those cases in which the rate of oxidation to the benzoic acid is relatively faster than the production of the aldehyde, a preponderance of acid results. This appears to be the case when p-nitrotoluene is employed.

As was previously stated, the yield of anisaldehyde depends upon maintaining a ratio of at least 2 to 1 methoxytoluene to anisaldehyde, and controlling the temperature at the beginning of the oxidation at somewhat less than 20° C, and preferably around 15° C. It is also of importance in this invention that the temperature at no time be allowed to rise above about 35° C, and that the acidity not advance substantially beyond 80 grams per liter, and preferably between 60 and 70 grams per liter of sulfuric acid. Under these conditions, and following the laboratory procedures described above, the tar content averages only about 30 to 40 grams, the anisic acid approximately 6 to 20 grams, and the anisaldehyde between about 700 and 750 grams. As was indicated hereinabove, by utilizing manganic sulfate, manganic hydroxy-sulfate, or sodium, potassium, aluminum or chromium manganic alums in the novel process of this invention, not only can anisaldehyde effectively be produced, but also a number of other benzaldehydes, as well as benzoic acids. For example, and as will be seen from the typical formulae and reactions set forth in Tables I and II, there can be produced p-methyl benzaldehyde, p-isopropyl benzaldehyde, p-chlorobenzaldehyde, o-chlorobenzaldehyde, dimethyl benzaldehyde, benzaldehyde, p-chlorobenzoic acid, o-chlorobenzoic acid, p-methylbenzoic acid, anisic acid, p-nitro benzoic acid, 2,4-dichlorobenzoic acid, p-sulfobenzoic acid, among others which will be apparent to those skilled in the art.

To illustrate the invention even further, there will now be described exemplary methods for preparing p-chlorobenzaldehyde and p-chlorobenzoic acid. To a 12 liter flask equipped with stirring apparatus, a water cooled condenser and a thermometer, there was added about 7 liters of 45% by weight of sulfuric acid and approximately 2 liters of settled manganic sludge, produced as earlier described. To the solution there was added with stirring 2000 grams of p-chlorotoluene and the temperature raised to 90° C and maintained at about this point until the sludge disappeared, which took approximately 18 hours. The liquid was then cooled and filtered, and the p-chlorobenzoic acid left on the filter for possible purification by recrystallization from water to produce high purity p-chlorobenzoic acid. The yield was 200 grams, and the product obtained had a melting point between 242° and 243° C.

Following further the above procedure, p-chlorobenzaldehyde may be obtained by distilling the separated organic liquid to produce about 600 grams of p-chlorobenzaldehyde having a boiling point of about 142° to 146° C. If the prime product desired is p-chlorobenzoic acid, the p-chlorobenzaldehyde need not be separated but can be reacted with more manganic sludge. As will now be manifest, if the sulfuric acid concentration is increased, a better yield of p-chlorobenzoic acid will result.

TABLE I
BENZALDEHYDES
p-methyl benzaldehyde
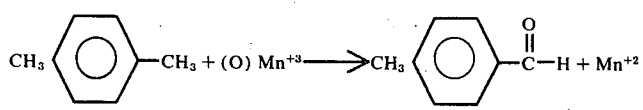
p-isopropyl benzaldehyde
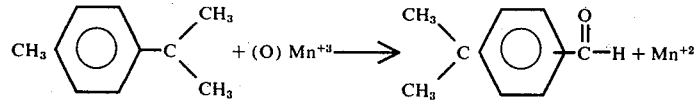
p-chlorobenzaldehyde
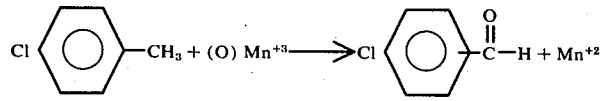
o-chlorobenzaldehyde
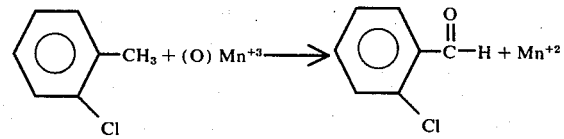
dimethyl benzaldehyde
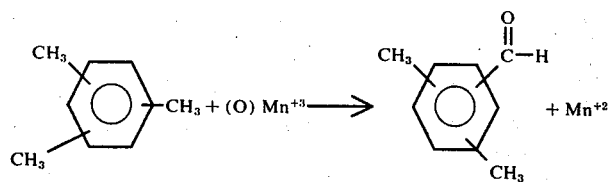
benzaldehyde
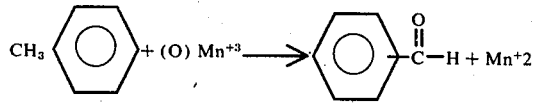
TABLE II
BENZOIC ACIDS
p-chlorobenzoic acid
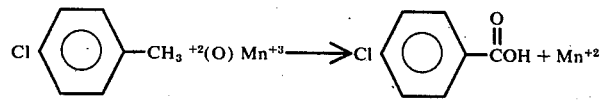
o-chlorobenzoic acid
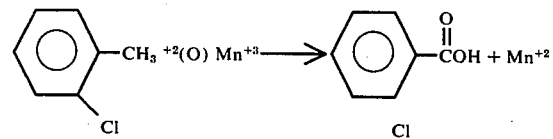
p-methyl benzoic acid
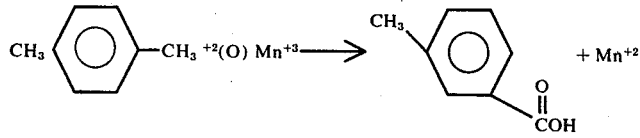
p-anisic acid
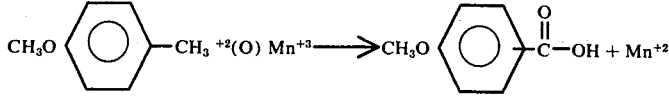
p-nitro benzoic acid
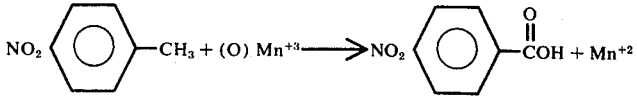

TABLE II-continued

BENZOIC ACIDS 2,4 dichlorobenzoic acid

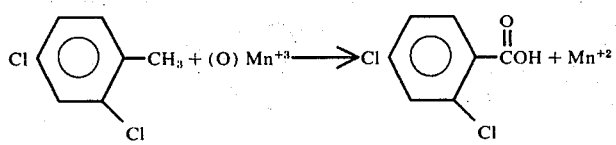

p-sulfonbenzoic acid

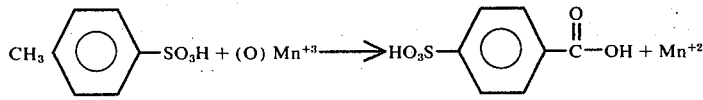

It is believed manifest from the foregoing description that there is provided by the present invention a novel process for the preparation of benzaldehydes and benzoic acids, and particularly anisaldehyde, wherein by utilization of potassium manganic alum or the sodium or chrome or aluminum alums a high yield of anisaldehyde with only a minimum of tars, a minimum of aromatic acids and a maximum utilization of the methoxytoluene for conversion to anisaldehyde. This is accomplished not only by utilization of the manganic salts disclosed, but by controlling the operating conditions so that at all times the acidity is within the range of 2½ to 8½ percent by weight of sulfuric acid and the temperature maintained so that throughout the oxidation process the temperature does not substantially exceed 30° C. It is to be further noted that in the instant process the cycle is essentially continuous with a portion of the manganic salt containing a plus 3 manganic valence ion being recycled to one or more electrolytic cells for re-oxidation, and a portion of the methoxytoluene returned to a storage vessel for subsequent introduction into the oxidation chamber.

Various changes have been disclosed in the processes and products of this invention, and these and other variations can be practiced in the invention without departing from the spirit thereof or the scope of the subjoined claims.

What is claimed is:

1. A method of producing anisaldehyde, which comprises introducing a manganic alum wherein the manganate ion has a plus 3 valence and is obtained by oxidizing in an electrolytic cell a mixture of manganese sulfate, potassium or sodium sulfate and sulfuric acid, into a reaction chamber containing approximately 8% by weight of sulfuric acid; adding to the chamber p-methoxytoluene; and while the oxidation proceeds, controlling the acid concentration to between about 2½ to 8½% by weight of sulfuric acid, the temperature within the reaction chamber to not substantially exceed more than about 30° C., and the ratio of para-methoxytoluene to anisaldehyde to between approximately 3 : 1 and not less than about 2 : 1, whereby anisaldehyde of relatively high purity is obtained with a consequent minimum level of tars and anisic acid.

2. A method of producing anisaldehyde as defined in claim 1, in which upon completion of the oxidation reaction the anisaldehyde produced is separated from the para-methoxytoluene and said excess para-methoxytoluene returned to the reaction chamber.

* * * * *